United States Patent [19]
Fourie

[11] Patent Number: 4,679,577
[45] Date of Patent: Jul. 14, 1987

[54] DEVICE FOR CLEANING TEETH

[76] Inventor: Phillippus J. Fourie, 34 Park Plaza, 21 Gregory Avenue, Melrose North, Johannesburg, Transvaal, South Africa

[21] Appl. No.: 744,855

[22] Filed: Jun. 14, 1985

[30] Foreign Application Priority Data

Jun. 15, 1984 [ZA] South Africa ................ 84/4529

[51] Int. Cl.$^4$ ............................................. A61C 15/00
[52] U.S. Cl. ................................................. 132/92 R
[58] Field of Search ...................... 132/91, 92, 92 R; 433/141

[56] References Cited

U.S. PATENT DOCUMENTS

| | | |
|---|---|---|
| 1,274,423 | 8/1918 | Kristmann ................ 132/92 R |
| 1,316,807 | 9/1919 | Ross . |
| 1,582,000 | 4/1926 | Gesell . |
| 1,644,390 | 10/1927 | Miller . |
| 1,952,358 | 3/1934 | Bohm . |
| 2,052,520 | 8/1936 | Sonnenberg . |
| 2,837,098 | 1/1958 | Sorboro . |
| 3,327,719 | 6/1967 | Ford . |
| 3,913,597 | 10/1975 | Day . |
| 3,915,178 | 10/1975 | Zellers . |
| 4,005,721 | 2/1977 | Yasumoto . |
| 4,495,956 | 1/1985 | Fourie . |

FOREIGN PATENT DOCUMENTS

| | | |
|---|---|---|
| 92433 | 11/1968 | France . |
| 78919 | 8/1951 | Norway . |
| 2040686 | 9/1980 | United Kingdom . |

*Primary Examiner*—Robert Peshock
*Attorney, Agent, or Firm*—Sughrue, Mion, Zinn, Macpeak, and Seas

[57] ABSTRACT

A flossing device comprising a floss carrying member having a hollow interior and a locking member receivable in the interior of the floss carrying member so as to be coaxially rotatable therein. The floss carrying member is adapted to support a span of dental floss. The locking member has an aperture therein through which the dental floss passes in an operative position of the locking member and the floss carrying member has an aperture therein, the arrangement being such that the aperture in the floss carrying member aligns with the aperture in the locking member in an operative arrangement of the two members. The apertures are such as to permit the floss to be introduced from the exterior of the floss carrying member into the aperture in the floss carrying member by laying the floss crosswise in said aperture from where the floss may be advanced, crosswise, into the aperture in the locking member.

5 Claims, 9 Drawing Figures

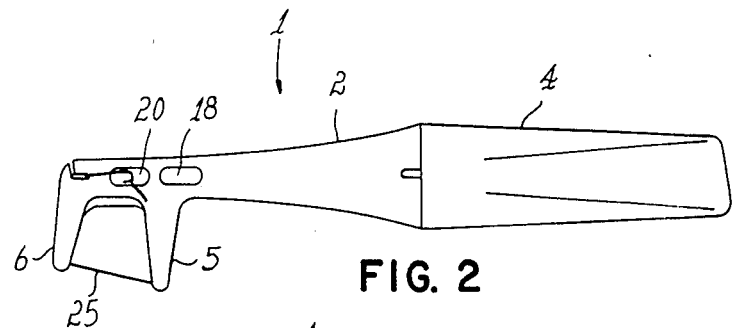
FIG. 2
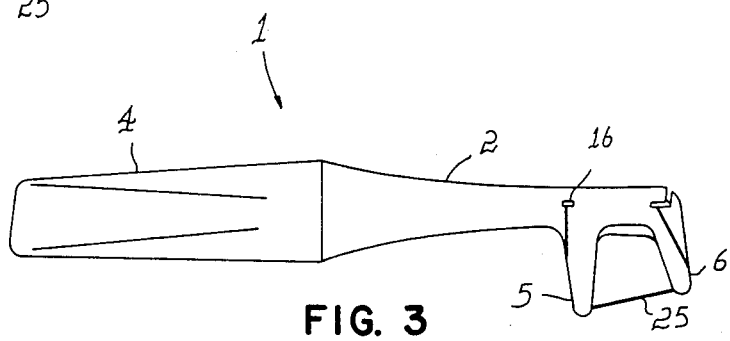
FIG. 3
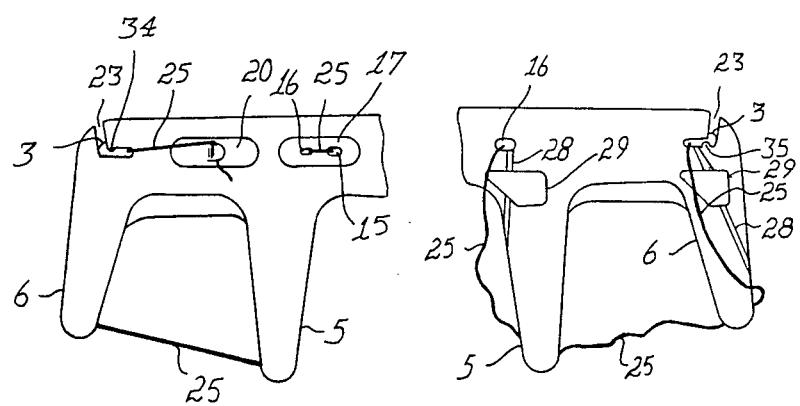
FIG. 4
FIG. 5

DEVICE FOR CLEANING TEETH

FIELD OF THE INVENTION

This invention relates to a device for cleaning teeth and more particularly to a device known in the art as a flossing device.

DESCRIPTION OF THE PRIOR ART

A flossing device is known which houses a roll or cocoon of dental floss. The device has a pair of arms or tines across which the floss is led to form a span. After use, the floss may be advanced and the used portion severed and discarded. Such a flossing device is described in my South African Pat. No. 82/7065, which has a U.S. equivalent, Ser. No. 426,131 filed Sep. 28, 1982, now U.S. Pat. No. 4,495,956.

A problem which is encountered with many flossing devices is that it is difficult to thread the floss through the relevant holes of the device, especially if the floss breaks during use.

It is accordingly an object of the invention to provide a flossing device in which the above problem is sought to be diminished.

SUMMARY OF THE INVENTION

A flossing device according to the invention comprises a floss carrying member having a hollow interior and a locking member receivable in the interior of the floss carrying member so as to be coaxially rotatable therein, the floss carrying member being adapted to support a span of dental floss, the locking member having an aperture therein through which the dental floss passes in an operative position of the locking member, the floss carrying member having an aperture therein, the arrangement being such that the aperture in the floss carrying member aligns with the aperture in the locking member in an operative arrangement of the two members, the apertures being such as to permit the floss to be introduced from the exterior of the floss carrying member into the aperture in the floss carrying member by laying the floss crosswise in said aperture from where the floss may be advanced, crosswise, into the aperture in the locking member.

Further according to the invention, the flossing device includes a housing member adapted to carry a stock of dental floss and adapted coaxially and rotatably to be connected to the floss carrying member, the housing member when so connected engaging the locking member so that rotation of the housing member relative to the floss carrying member causes rotation of the locking member.

Further according to the invention, the aperture in the locking member comprises a slot located in the leading end of the locking member, the slot extending from the exterior of the floss carrying member to its interior.

Further according to the invention, the floss carrying member has a forward tine and a rearward tine projecting therefrom, the tines being adapted to support the span of floss, the slot in the floss carrying member being located in the region of the base of the forward tine.

Further according to the invention, the floss carrying member has an opening through it at the base of the rearward tine and the locking member has an opening through it aligning with the opening in the floss carrying member in an operative position of the locking member, the arrangement permitting the floss to be threaded through the openings in the floss carrying member and locking member respectively and thence across the tines of the floss carrying member, from where the floss may be passed through the slots in the floss carrying member and locking member respectively.

DESCRIPTION OF PREFERRED EMBODIMENT OF THE INVENTION

A preferred embodiment of the invention will now be described by way of example with reference to the accompanying drawings in which:

FIGS. 2 and 3 are elevations of the flossing device in assembled form seen from opposite sides thereof;

FIGS. 4 and 5 are enlarged elevations of portions of the device of FIGS. 2 and 3.

Figure 1A:
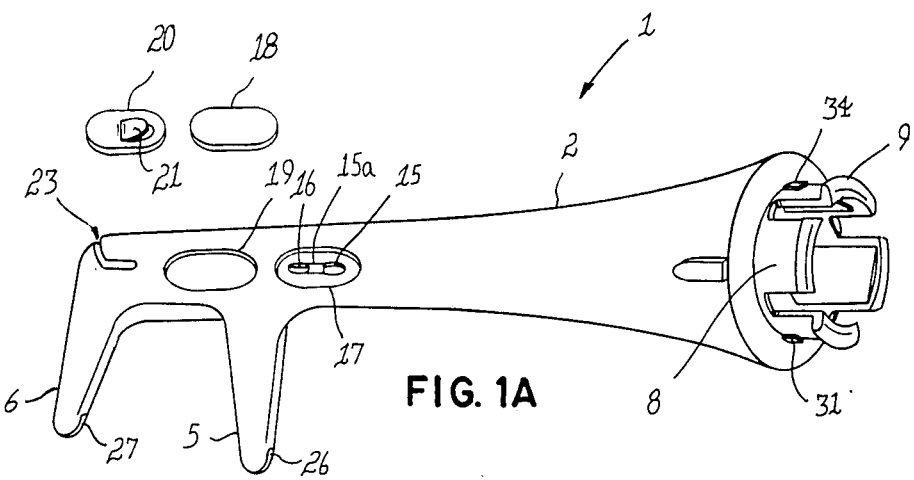
FIGS. 1A–1C show respective views of parts of a flossing device according to the invention.
Figure 1B:
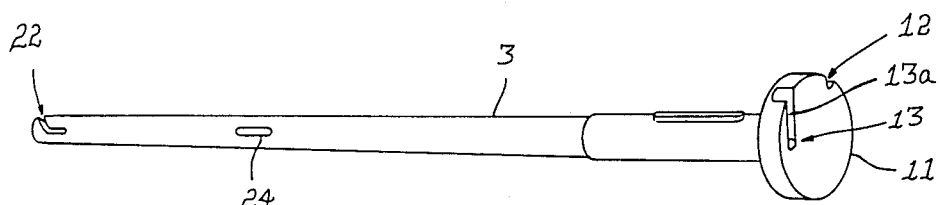

The flossing device 1 shown in the drawings comprises three principal parts—a floss carrying member 2, a locking member 3 and a housing 4. The floss carrying member 2 has a hollow interior adapted to receive the locking member 3 so that the locking member is coaxially rotatable therein.

At one end the floss carrying member 2 has a rearward tine 5 and a forward tine 6 adapted to support a span of dental floss, and at its opposite end it has an annular castelled ring-like projection 8 terminating in an annular shoulder 9.

The housing member 4 has a hollow interior which is adapted to house a roll or cocoon of dental floss (not shown). At its open end the housing member 4 has an annular recess 10 in its interior. The floss carrying member 2 and the housing member 4 are so constructed that they can be snapped into engagement with one another, with the annular shoulder 9 of the floss carrying member seating in the recess 10 of the housing member.

The locking member 3 has a head 11 at one end which seats on the ring-like projection 8 of the floss carrying member 2 when the locking member is operatively located therein. When the floss carrying member 2 is engaged with the housing 4, the locking member 3 can be so oriented that a notch 12 on its head 11 accommodates a longitudinal rib 14 provided in the interior of the housing member 4. With the rib 14 trapped in the notch 12, axial rotation of the housing 4 relative to the floss carrying member 2 will cause the locking member 3 to rotate within the floss carrying member.

The head 11 of the locking member 3 has a hole 13 through it from which a groove 13a extends to the periphery of the head.

The floss carrying member 2 has an opening 15 in its side wall and a second opening 16 adjacent the opening 15. The opening 16 extends through the opposite side wall of the floss carrying member as well. The openings 15, 16 are located within a shallow oval shaped recess 17. A plug 18 is provided which when pressed into the recess 17 forms a tight fit therein to close the holes 15, 16. A narrow channel 15a connects the openings 15, 16.

A second shallow oval shaped recess 19 is located adjacent the recess 17 and is adapted similarly to receive a metal insert 20 having a cutting edge 21.

The leading end of the locking member 3 has a narrow slot 22 therein comprising an inclined section extending inwardly from the edge of the member and a horizontal section extending coaxially with the member. A complementary slot 23 is formed in the floss carrying member 2 at the base of the forward tine 6, the slot 23 extending from the exterior of the member to its interior. When the locking member 3 is operatively located in a given orientation in the floss carrying member 2, the slots 22, 23 are in register with one another. An opening 24 is provided in the locking member 3 extending through it and spaced from its leading end.

In order to thread the flossing device with floss 25, a free end of the floss is led from the roll of floss (not shown) in the housing member 10, whilst the device is disassembled. The free end of the floss is passed along the groove 13a in the head of the locking member 3 and through the hole 13. The free end of the floss is then led into the interior of the floss carrying member and with the aid of a needle (not shown) or the like, is passed from the interior of the floss carrying member 2 through the opening 15. The locking member 3 is then inserted into the floss carrying member 2 so that the opening 24 aligns with the opening 16 in the floss carrying member. In this position, the slots 22, 23 will also align with one another. The free end of the floss is thereupon passed through the openings 16, 24 to emerge from the opposite side of the floss carrying member 2. In this position the floss lies in the channel 15a connecting openings 15, 16. The floss is then led across the tines 5, 6 to form a span between the tines (FIGS. 2, 3 and 4). For this purpose the free ends of the tines, 5, 6 have shallow recesses 26, 27 therein (FIG. 1A). The floss 25 is then fed in crosswise fashion, into the slot 23 of the floss carrying member 2 from where it is advanced, also in crosswise fashion, into the slot 22 of the locking member.

In order to protect the floss 25 as much as possible from exterior soiling, narrow channels 28 may be formed in the tines 5, 6 leading towards the recesses 26, 27 in the free ends of the tines and wherein the floss lies in an operative position (FIG. 5). Hollows 29 may be formed in the bases of the tines 5, 6 during the injection moulding process for known purposes.

Figure 1C:
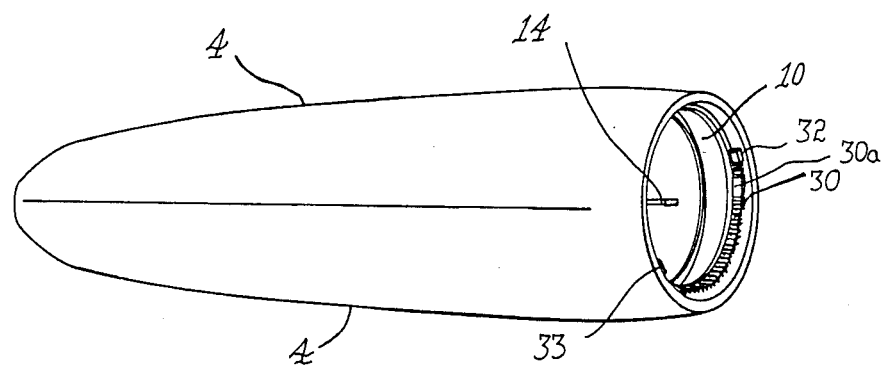
Figure 6A:
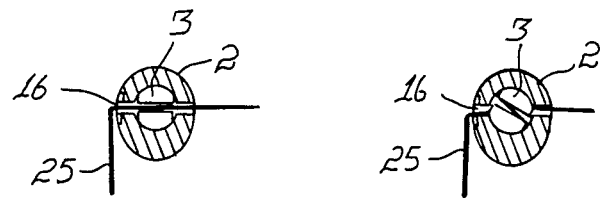
FIGS. 6A–6B are views illustrating the locking and tautening action of the device.
Figure 6B:
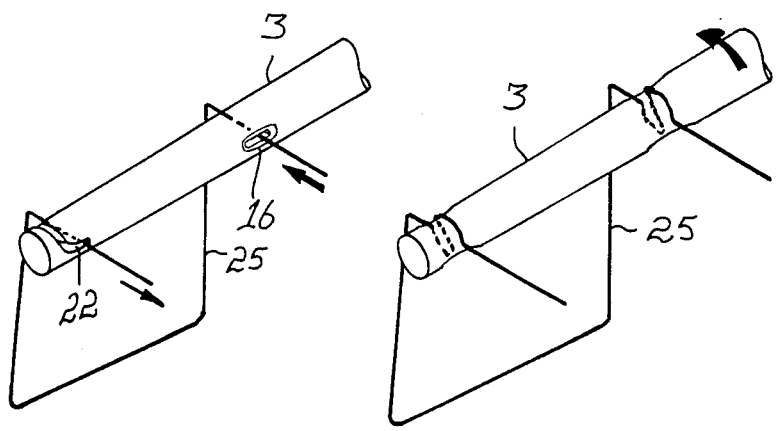

In order to tauten and lock the span of floss, the housing member 4 is rotated relative to the floss carrying member 2. This causes the floss to encircle the locking member 3 as illustrated in FIG. 6B. The locking member 3 may be narrowed in the regions where the floss encircles it, namely in the region of the opening 24 and the slot 22, as shown in FIG. 6B. To provide suitable resistance to rotation of the housing member relative to the floss carrying member 2, the housing member 4 may have a serrated track 30 (FIG. 1C) adapted to be contacted by a formation 31 on the floss carrying member 2. The arrangement may be one in which the formation 31 "clicks" into position when the limit of rotation of the housing member 4 in the tautening direction is reached. Such limit may be provided by a stop member 32 on the housing member 4. The serrated track 30 may be slightly built up as indicated by the numeral 30a to permit the formation 31 to "click" into a locked position. A similar stop member 33 may be provided to limit rotation of the housing member 4 in the loosening direction and a further lug 34 may be provided on the floss carrying member for this purpose. Once the span has been tautened, excess or used floss may be cut off on the cutting edge 21 of the metal insert 20.

The provision of the slots 22, 23 enable the flossing device easily to be re-threaded, especially if the floss 25 breaks across the span. In order to serve to retain the floss in the slot 22 of the locking member, pimples 34, 35 may be provided on opposite sides of the slot 23 of the floss carrying member 2. (FIGS. 4, 5).

Many other embodiments of the invention may be made differing in matters of detail only from that described above and without departing from the scope of the invention described in the appended claims.

I claim:

1. A flossing device, comprising: an elongate floss carrying member (2) having a hollow interior and an open first end, an elongate locking member (3) inserted into the hollow interior of the floss carrying member through said open first end and coaxially rotatable therein, a second, opposite end of the floss carrying member defining two spaced, laterally extending tines (5, 6) supporting a span (25) of dental floss between outer ends thereof, the locking member having a first open ended slot (22) extending transversely through and across an inner end thereof and through which the dental floss passes in an operative position of the locking member, the floss carrying member having a second open ended slot (23) extending transversely through and across said opposite end thereof, wherein the first and second slots are in aligned registry in a threading position of the locking member relative to the floss carrying member such that an advanced length of floss may be introduced from the exterior of the device into inner, bottom portions of the slots by laying the floss crosswise in said open slot ends and advancing the floss deeper into the slots, whereafter the locking member may be rotated within the floss carrying member to wind the floss around the locking member and thereby tension the span between the tines.

2. A flossing device as claimed in claim 1 further including a housing member 4 adapted to carry a stock of dental floss and adapted coaxially and rotatably to be connected to the floss carrying member, the housing member when so connected engaging the locking member so that rotation of the housing member relative to the floss carrying member causes rotation of the locking member.

3. A flossing device as claimed in claim 1 or 2 in which one of the tines is a forward tine and the other tine is a rearward tine, the forward tine being positioned nearer said opposite end, the second open ended slot in the floss carrying member being located in the region of the base of the forward tine.

4. A flossing device as claimed in claim 3 in which the floss carrying member has a first opening through it at the base of the rearward tine and the locking member has a second opening through it in aligned registry with the first opening in the floss carrying member in the threading position of the locking member, the arrangement permitting the floss to be threaded through the first and second openings in the floss carrying member and locking member respectively and thence across the tines of the floss carrying member from where the floss may be passed through the open ended slots in the floss carrying member and locking member respectively.

5. A flossing device as claimed in claim 4, wherein the locking member has a narrower portion in a vicinity of the second opening, and in a vicinity of a leading end of the second open ended slot.

* * * * *